(12) United States Patent
Edwards et al.

(10) Patent No.: US 7,449,020 B2
(45) Date of Patent: Nov. 11, 2008

(54) METHOD FOR TREATING A SPHINCTER

(75) Inventors: Stuart D Edwards, Salinas, CA (US);
David S Utley, Redwood City, CA (US);
Ronald G Lax, Palm City, FL (US);
John Gaiser, Mountain View, CA (US)

(73) Assignee: Curon Medical, Inc., Hercules, CA (US)

( * ) Notice: Subject to any disclaimer, the term of this patent is extended or adjusted under 35 U.S.C. 154(b) by 429 days.

(21) Appl. No.: 11/079,697

(22) Filed: Mar. 14, 2005

(65) Prior Publication Data
US 2005/0159743 A1 Jul. 21, 2005

Related U.S. Application Data

(60) Division of application No. 10/254,471, filed on Sep. 25, 2002, now Pat. No. 6,866,663, which is a continuation of application No. 09/090,794, filed on Jun. 4, 1998, now abandoned, which is a continuation-in-part of application No. 09/032,367, filed on Feb. 27, 1998, now Pat. No. 6,044,846, application No. 11/079,697, and a continuation-in-part of application No. 09/921,356, filed on Aug. 2, 2001, now Pat. No. 6,613,047, which is a continuation of application No. 09/032,366, filed on Feb. 27, 1998, now abandoned.

(51) Int. Cl.
*A61B 18/18* (2006.01)
(52) U.S. Cl. .......................... 606/28; 128/898; 607/133
(58) Field of Classification Search ............ 606/27–31, 606/41, 45–50; 607/101, 102, 116, 133; 600/500, 506; 128/898
See application file for complete search history.

(56) References Cited

U.S. PATENT DOCUMENTS 1,798,902 A 3/1931 Raney (Continued)

FOREIGN PATENT DOCUMENTS

DE 43 03 882 A 2/1995

(Continued)

OTHER PUBLICATIONS

Dallemagne, B., et al. "Laparoscopic Nissen Fundoplication: Preliminary Report." *Surgical Laparoscopy & Endoscopy.* 1991. 1(3): 138-43.

(Continued)

*Primary Examiner*—Michael Peffley
(74) *Attorney, Agent, or Firm*—Ryan Kromholz & Manion S.C.

(57) ABSTRACT

A method for treating a sphincter provides a polymer material having a liquid state. The method also provides a catheter having a distal end, a tissue piercing device carried by the distal end, and an energy delivery device coupled to the tissue piercing device. The tissue piercing device has a lumen. The method introduces the catheter into an esophagus and pierces an exterior sphincter tissue surface within with the tissue piercing device. The method advances the tissue piercing device into an interior sphincter tissue site and conveys the polymer material while in a liquid state through the lumen into the interior sphincter tissue site. The method delivers energy to the tissue piercing device to transform the polymer material into a less liquid state within the interior sphincter tissue site, to thereby remodel the sphincter.

17 Claims, 15 Drawing Sheets

U.S. PATENT DOCUMENTS

| | | |
|---|---|---|
| 3,517,128 A | 6/1970 | Hines |
| 3,901,241 A | 8/1975 | Allen, Jr. ................. 128/303.1 |
| 4,011,872 A | 3/1977 | Komiya ................. 128/303.14 |
| 4,196,724 A | 4/1980 | Wirt et al. ................... 128/136 |
| 4,411,266 A | 10/1983 | Cosman ................. 128/303.18 |
| 4,423,812 A | 1/1984 | Sato .......................... 206/387 |
| 4,532,924 A | 8/1985 | Auth et al. ............. 128/303.17 |
| 4,565,200 A | 1/1986 | Cosman ....................... 128/642 |
| 4,705,041 A | 11/1987 | Kim |
| 4,901,737 A | 2/1990 | Toone ......................... 128/848 |
| 4,906,203 A | 3/1990 | Margrave et al. ............. 439/188 |
| 4,907,589 A | 3/1990 | Cosman ........................ 606/34 |
| 4,943,290 A | 7/1990 | Rexroth et al. ................. 606/45 |
| 4,947,842 A | 8/1990 | Marchosky et al. ......... 128/401 |
| 4,955,377 A | 9/1990 | Lennox et al. |
| 4,966,597 A | 10/1990 | Cosman ........................ 606/50 |
| 4,976,711 A | 12/1990 | Parins et al. ................... 606/48 |
| 5,019,075 A | 5/1991 | Spears et al. |
| 5,035,696 A | 7/1991 | Rydell ........................... 606/47 |
| 5,046,512 A | 9/1991 | Murchie ...................... 128/848 |
| 5,047,028 A | 9/1991 | Qian |
| 5,057,107 A | 10/1991 | Parins et al. ................... 606/48 |
| 5,078,717 A | 1/1992 | Parins et al. ................... 606/48 |
| 5,083,565 A | 1/1992 | Parins ......................... 128/642 |
| 5,084,044 A | 1/1992 | Quint |
| 5,088,979 A | 2/1992 | Filipi et al. ..................... 604/26 |
| 5,094,233 A | 3/1992 | Brennan ......................... 602/6 |
| 5,100,423 A | 3/1992 | Fearnot ....................... 606/159 |
| 5,106,360 A | 4/1992 | Ishiwara et al. |
| 5,122,137 A | 6/1992 | Lennox ......................... 606/40 |
| 5,125,928 A | 6/1992 | Parins et al. ................... 606/48 |
| 5,156,151 A | 10/1992 | Imran |
| 5,190,541 A | 3/1993 | Abele et al. .................... 606/46 |
| 5,197,963 A | 3/1993 | Parins ........................... 606/46 |
| 5,197,964 A | 3/1993 | Parins ........................... 606/48 |
| 5,205,287 A | 4/1993 | Erbel et al. ................... 128/632 |
| 5,215,103 A | 6/1993 | Desai ........................... 128/784 |
| 5,232,444 A | 8/1993 | Just et al. |
| 5,236,413 A | 8/1993 | Feiring |
| 5,242,441 A | 9/1993 | Avitall |
| 5,254,126 A | 10/1993 | Filipi et al. .................. 606/146 |
| 5,256,138 A | 10/1993 | Burek et al. ................... 606/42 |
| 5,257,451 A | 11/1993 | Edwards et al. ................ 29/825 |
| 5,263,493 A | 11/1993 | Avitall |
| 5,275,162 A | 1/1994 | Edwards et al. ............. 128/642 |
| 5,275,608 A | 1/1994 | Forman et al. ............... 606/170 |
| 5,275,610 A | 1/1994 | Eberbach |
| 5,277,201 A | 1/1994 | Stern ........................... 607/98 |
| 5,281,216 A | 1/1994 | Klicek .......................... 606/42 |
| 5,281,217 A | 1/1994 | Edwards et al. ................ 606/41 |
| 5,281,218 A | 1/1994 | Imran ........................... 606/41 |
| 5,290,286 A | 3/1994 | Parins ........................... 606/50 |
| 5,292,321 A | 3/1994 | Lee |
| 5,293,869 A | 3/1994 | Edwards et al. ............. 128/642 |
| 5,309,910 A | 5/1994 | Edwards et al. ............. 128/642 |
| 5,313,943 A | 5/1994 | Houser et al. ............... 128/642 |
| 5,314,466 A | 5/1994 | Stern et al. .................. 607/156 |
| 5,316,020 A | 5/1994 | Truffer ........................ 128/848 |
| 5,324,284 A | 6/1994 | Imran |
| 5,328,467 A | 7/1994 | Edwards et al. ................ 604/95 |
| 5,334,196 A | 8/1994 | Scott et al. ................... 606/138 |
| 5,336,222 A | 8/1994 | Durgin, Jr. et al. |
| 5,345,936 A | 9/1994 | Pomeranz et al. |
| 5,348,554 A | 9/1994 | Imran et al. ................... 606/41 |
| 5,363,861 A | 11/1994 | Edwards et al. ............. 128/772 |
| 5,365,926 A | 11/1994 | Desai ......................... 128/642 |
| 5,365,945 A | 11/1994 | Halstrom ..................... 128/848 |
| 5,366,490 A | 11/1994 | Edwards et al. ............. 607/99 |
| 5,368,557 A | 11/1994 | Nita et al. ..................... 604/22 |
| 5,368,592 A | 11/1994 | Stern et al. .................... 606/33 |
| 5,370,675 A | 12/1994 | Edwards et al. |
| 5,370,678 A | 12/1994 | Edwards et al. ............. 607/101 |
| 5,383,876 A | 1/1995 | Nardella ....................... 606/49 |
| 5,383,917 A | 1/1995 | Desai ......................... 607/702 |
| 5,385,544 A | 1/1995 | Edwards et al. ............. 604/22 |
| 5,397,339 A | 3/1995 | Desai ......................... 687/116 |
| 5,398,683 A | 3/1995 | Edwards et al. ............. 128/642 |
| 5,401,272 A | 3/1995 | Perkins ........................ 606/15 |
| 5,403,311 A | 4/1995 | Abele et al. .................. 606/49 |
| 5,409,453 A | 4/1995 | Lundquist et al. ............. 604/22 |
| 5,409,483 A | 4/1995 | Campbell et al. |
| 5,415,657 A | 5/1995 | Taymor-Luria |
| 5,421,819 A | 6/1995 | Edwards et al. ............. 604/22 |
| 5,423,808 A | 6/1995 | Edwards et al. ............. 606/34 |
| 5,423,811 A | 6/1995 | Imran et al. ................... 606/41 |
| 5,423,812 A | 6/1995 | Ellman et al. ................. 606/45 |
| 5,433,739 A | 7/1995 | Sluijter et al. ................ 607/99 |
| 5,435,805 A | 7/1995 | Edwards et al. ............. 604/22 |
| 5,441,499 A | 8/1995 | Fritzsch ....................... 606/45 |
| 5,443,470 A | 8/1995 | Stern et al. |
| 5,451,406 A * | 9/1995 | Lawin et al. ................ 424/423 |
| 5,454,782 A | 10/1995 | Perkins |
| 5,456,662 A | 10/1995 | Edwards et al. ............. 604/22 |
| 5,456,682 A | 10/1995 | Edwards et al. ............. 606/31 |
| 5,458,596 A | 10/1995 | Lax et al. ..................... 606/31 |
| 5,458,597 A | 10/1995 | Edwards et al. ............. 606/41 |
| 5,465,717 A | 11/1995 | Imran |
| 5,470,308 A | 11/1995 | Edwards et al. ............. 604/22 |
| 5,471,982 A | 12/1995 | Edwards et al. ............. 128/642 |
| 5,472,441 A | 12/1995 | Edwards et al. ............. 606/41 |
| 5,484,400 A | 1/1996 | Edwards et al. ............. 604/22 |
| 5,486,161 A | 1/1996 | Lax et al. ..................... 604/22 |
| 5,490,984 A | 2/1996 | Freed .......................... 424/436 |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. ................. 606/39 |
| 5,505,730 A | 4/1996 | Edwards ...................... 606/41 |
| 5,507,743 A | 4/1996 | Edwards et al. ............. 606/41 |
| 5,509,419 A | 4/1996 | Edwards et al. ............. 128/642 |
| 5,514,130 A | 5/1996 | Baker .......................... 606/41 |
| 5,514,131 A | 5/1996 | Edwards et al. ............. 606/45 |
| 5,520,684 A | 5/1996 | Imran .......................... 606/41 |
| 5,531,676 A | 7/1996 | Edwards et al. ............. 604/22 |
| 5,531,677 A | 7/1996 | Lundquist et al. ............. 604/22 |
| 5,536,240 A | 7/1996 | Edwards et al. ............. 604/22 |
| 5,536,267 A | 7/1996 | Edwards et al. ............. 606/41 |
| 5,540,655 A | 7/1996 | Edwards et al. ............. 604/22 |
| 5,542,915 A | 8/1996 | Edwards et al. ............. 604/22 |
| 5,542,916 A | 8/1996 | Hirsch et al. ................. 604/22 |
| 5,545,161 A | 8/1996 | Imran .......................... 606/41 |
| 5,545,171 A | 8/1996 | Sharkey et al. ............. 606/148 |
| 5,545,193 A | 8/1996 | Fleischman et al. ........... 607/99 |
| 5,545,434 A | 8/1996 | Huarng ....................... 427/243 |
| 5,549,108 A | 8/1996 | Edwards et al. ............. 128/642 |
| 5,549,644 A | 8/1996 | Lundquist et al. ............. 604/22 |
| 5,554,110 A | 9/1996 | Edwards et al. ............. 604/22 |
| 5,556,377 A | 9/1996 | Rosen et al. ................. 604/22 |
| 5,558,672 A | 9/1996 | Edwards et al. ............. 606/41 |
| 5,558,673 A | 9/1996 | Edwards et al. ............. 606/41 |
| 5,562,720 A | 10/1996 | Stern et al. |
| 5,571,116 A | 11/1996 | Bolanos et al. ............. 606/139 |
| 5,578,007 A | 11/1996 | Imran |
| 5,588,432 A | 12/1996 | Crowley |
| 5,588,960 A * | 12/1996 | Edwards et al. ............. 604/20 |
| 5,599,345 A | 2/1997 | Edwards et al. ............. 606/41 |
| 5,609,151 A | 3/1997 | Mulier et al. ............... 128/642 |
| 5,624,439 A | 4/1997 | Edwards et al. ............. 606/45 |
| 5,672,153 A | 9/1997 | Lax et al. |
| 5,676,674 A | 10/1997 | Bolanos et al. ............. 606/139 |
| 5,686,425 A | 11/1997 | Lee |
| 5,688,266 A | 11/1997 | Edwards et al. |
| 5,688,490 A | 11/1997 | Tournier et al. ............ 424/9.52 |
| 5,702,438 A | 12/1997 | Avitall |

| | | | |
|---|---|---|---|
| 5,709,224 A | 1/1998 | Behl et al. | |
| 5,732,698 A | 3/1998 | Swanson et al. | |
| 5,738,096 A | 4/1998 | Ben-Haim | |
| 5,830,210 A | 11/1998 | Rudko et al. | |
| 5,830,213 A | 11/1998 | Panescu et al. | |
| 5,836,874 A | 11/1998 | Swanson et al. | |
| 5,860,974 A | 1/1999 | Abele | |
| 5,871,483 A | 2/1999 | Jackson et al. | |
| 6,033,401 A | 3/2000 | Edwards et al. | |
| 6,044,846 A | 4/2000 | Edwards | |
| 6,073,052 A | 6/2000 | Zelickson et al. | |
| 6,098,629 A * | 8/2000 | Johnson et al. | 128/897 |
| 6,238,335 B1 | 5/2001 | Silverman et al. | |
| 6,251,063 B1 | 6/2001 | Silverman et al. | |
| 6,251,064 B1 | 6/2001 | Silverman et al. | |
| 6,358,197 B1 | 3/2002 | Silverman et al. | |
| 6,613,047 B2 | 9/2003 | Edwards | |
| 6,666,848 B2 * | 12/2003 | Stone | 604/164.01 |
| 2002/0082610 A1 | 6/2002 | Cioanta et al | |

FOREIGN PATENT DOCUMENTS

| | | |
|---|---|---|
| DE | 38 38 840 A | 2/1997 |
| EP | 0 139 607 A1 | 5/1985 |
| EP | 0 608 609 A2 | 8/1994 |
| WO | WO 91/01773 | 2/1991 |
| WO | 92/10142 | 6/1992 |
| WO | 93/08755 | 5/1993 |
| WO | 94/10925 | 5/1994 |
| WO | 95/19142 | 7/1994 |
| WO | WO 94/21165 | 9/1994 |
| WO | WO 94/21178 | 9/1994 |
| WO | WO 94/22366 | 10/1994 |
| WO | 94/26178 | 11/1994 |
| WO | 95/18575 | 7/1995 |
| WO | 95/25472 | 9/1995 |
| WO | WO 96/00042 | 1/1996 |
| WO | WO 96/16606 | 6/1996 |
| WO | 96/29946 | 10/1996 |
| WO | WO 97/06857 | 2/1997 |
| WO | WO 97/43971 | 2/1997 |
| WO | WO 97/32532 | 9/1997 |

OTHER PUBLICATIONS

Hinder, R. A., et al. "The Technique of Laparoscopic Nissen Fundoplication." *Surgical Laparoscopy & Endoscopy.* 1992. 1992. 2(3): 265-272.

Karlstrom, L. H. et al. "Ectopic jejunal pacemakers and enterogastric reflux after Roux gastrectomy: Effect of intestinal pacing." *Surgery.* 1989. 106(3): 486-495.

Kelly, K. A., et al. "Duodenal-gastric reflux and slowed gastric emptying by electrical pacing of the canine duodenal pacesetter potential." *Gastroenterology.* 1977. 72(3):429-33.

Urschel, J. D. "Complications of Antireflux Surgery." *Am J Surg.* 1993. 166(1): 68-70.

Kaneko, et al., *Physiological Laryngeal Pacemaker,* May 1985, Trans Am Soc Artif Intern Organs, vol. XXXI, pp. 293-296.

Mugica, et al., *Direct Diaphragm Stimulation,* Jan. 1987, PACE, vol. 10, pp. 252-256.

Mugica, et al., *Neurostimulation: An Overview,* Chapter 21, *Preliminary Test of a Muscular Diaphragm Pacing System on Human Patients,* 1985, pp. 263-279.

Nochomovitz, et al., *Electrical Activation of the Diaphragm,* Jun. 1988, Clinics in Chest Medicine, vol. 9, No. 2, pp. 349-358.

Prior, et al., *Treatment of Menorrhagia by Radiofrequency Heating,* 1991, Int. J. Hyperthermia, vol. 7, pp. 213-220.

Rice, et al., *Endoscopic Paranasal Sinus Surgery,* Chapters 5, *Functional Endoscopic Paranasal Sinus Surgery, The Technique of Messerklinger,* Raven Press, 1988, pp. 75-104.

Rice, et al., *Endoscopic Paranasal Sinus Surgery,* Chapters 6, *Total Endoscopic Sphenoethmoidectomy, The Technique of Wigand,* Raven Press, 1988, pp. 105-125.

* cited by examiner

METHOD FOR TREATING A SPHINCTER

RELATED APPLICATIONS

This application is a divisional of U.S. patent application Ser. No. 10/254,471, filed 25 Sep. 2002 (now U.S. Pat. No. 6,866,663), which is a continuation of U.S. patent application Ser. No. 09/090,794, filed Jun. 4, 1998 (now abandoned), which is a continuation-in-part of U.S. patent application Ser. No. 09/032,367, filed Feb. 27, 1998 (now U.S. Pat. No. 6,044,846), and a continuation-in-part of U.S. patent application Ser. No. 09/921,356, filed Aug. 2, 2001 (now U.S. Pat. No. 6,613,047), which is a continuation of U.S. patent application Ser. No. 09/032,366, filed Feb. 27, 1998 (now abandoned).

FIELD OF THE INVENTION

This invention relates generally to an apparatus to treat sphincters, and more particularly to an apparatus to treat esophageal sphincters.

DESCRIPTION OF RELATED ART

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: Gastroesophageal Reflux Disease: Current Strategies For Patient Management. Arch Fam Med, 5(4): 221-7; (1996 April)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20-30% of patients over age 65. Moreover, GERD causes adenocarcinoma, or cancer of the esophagus, which is increasing in incidence faster than any other cancer (Reynolds J C: Influence Of Pathophysiology, Severity, And Cost On The Medical Management Of Gastroesophageal Reflux Disease. Am J Health Syst Pharm, 53(22 Suppl 3):S5-12 (1996 Nov. 15)).

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, JD: Complications Of Antireflux Surgery, Am J Surg 166(1): 68-70; (1993 July)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. Surgical Laparoscopy and Endoscopy, Vol. 1, No. 3, (1991), pp. 138-43 and by Hindler et al. Surgical Laparoscopy and Endoscopy, Vol. 2, No. 3, (1992), pp. 265-272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure, an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction.

Besides the LES, there are other sphincters in the body which if not functioning properly can cause disease states or otherwise adversely affect the lifestyle of the patient. Reduced muscle tone or otherwise aberrant relaxation of sphincters can result in a laxity of tightness disease states including but not limited to urinary incontinence.

There is a need to provide an apparatus to remodel a sphincter. Another need exists for an apparatus to deliver a polymer material into a sphincter wall and deliver sufficient energy to the polymer material to increase a wall thickness of the sphincter. There is a further need for an apparatus to controllably reduce a diameter of a sphincter without creating a permanent impairment of the sphincter's ability to achieve a physiologically normal state of closure. Still a further need exists for an apparatus to deliver energy to a sphincter wall and create a tightening of a sphincter without permanently damaging anatomical structures near the sphincter. There is still another need for an apparatus to reduce the diameter of a lower esophageal sphincter to reduce a frequency of reflux of stomach contents into an esophagus.

SUMMARY OF THE INVENTION

One aspect of the invention provides a method for treating a sphincter. The method provides a polymer material having a liquid state. The method also provides a catheter having a distal end, a tissue piercing device carried by the distal end, and an energy delivery device coupled to the tissue piercing device. The tissue piercing device has a lumen. The method introduces the catheter into an esophagus and pierces an exterior sphincter tissue surface within with the tissue piercing device. The method advances the tissue piercing device into an interior sphincter tissue site and conveys the polymer material while in a liquid state through the lumen into the interior sphincter tissue site. The method delivers energy to the tissue piercing device to transform the polymer material into a less liquid state within the interior sphincter tissue site, to thereby remodel the sphincter.

In one embodiment, the method delivers energy to the tissue piercing device to create controlled cell necrosis in the sphincter.

In one embodiment, the method provides a cooling medium and conveys the cooling medium into contact with the exterior sphincter tissue surface pierced by the tissue piercing device.

The polymer material can comprise, e.g., collagen or silicone.

DETAILED DESCRIPTION

Figure 1A:
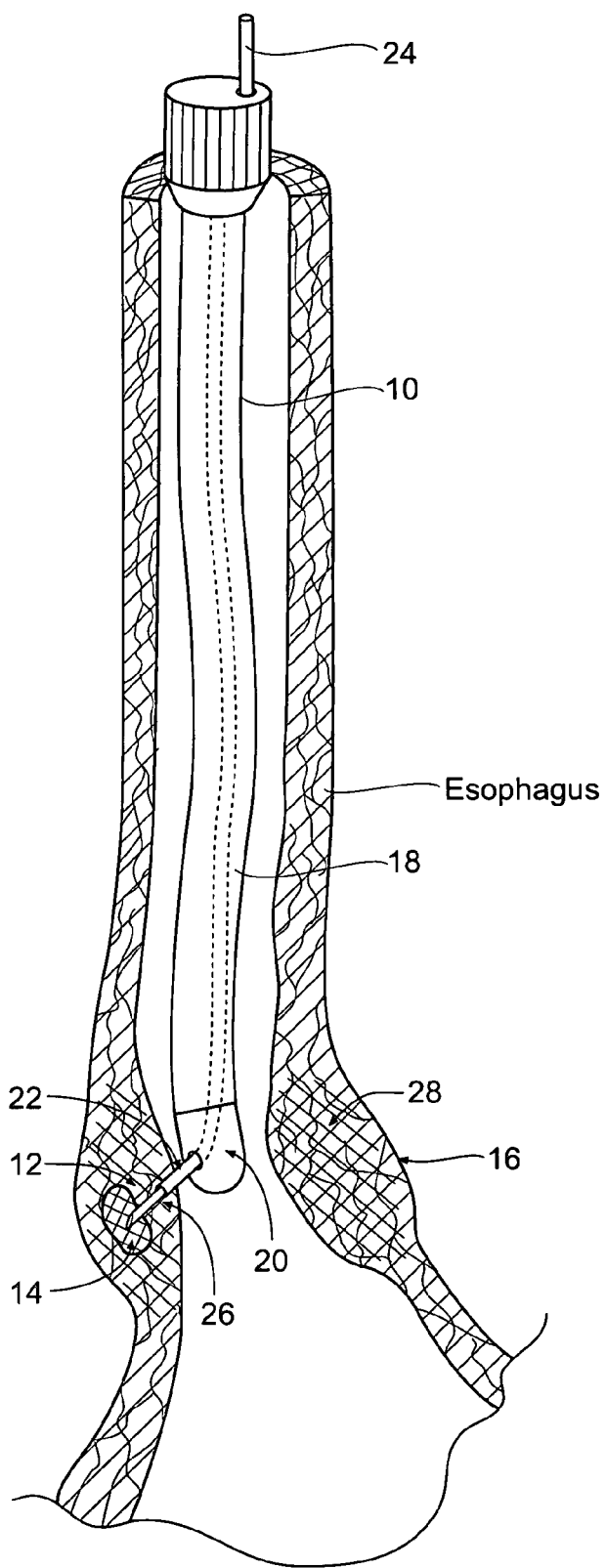
FIG. 1A is an illustrated lateral view of the upper GI tract illustrating the positioning of the sphincter treatment apparatus of the present invention in the lower esophageal sphincter.
Figure 1B:
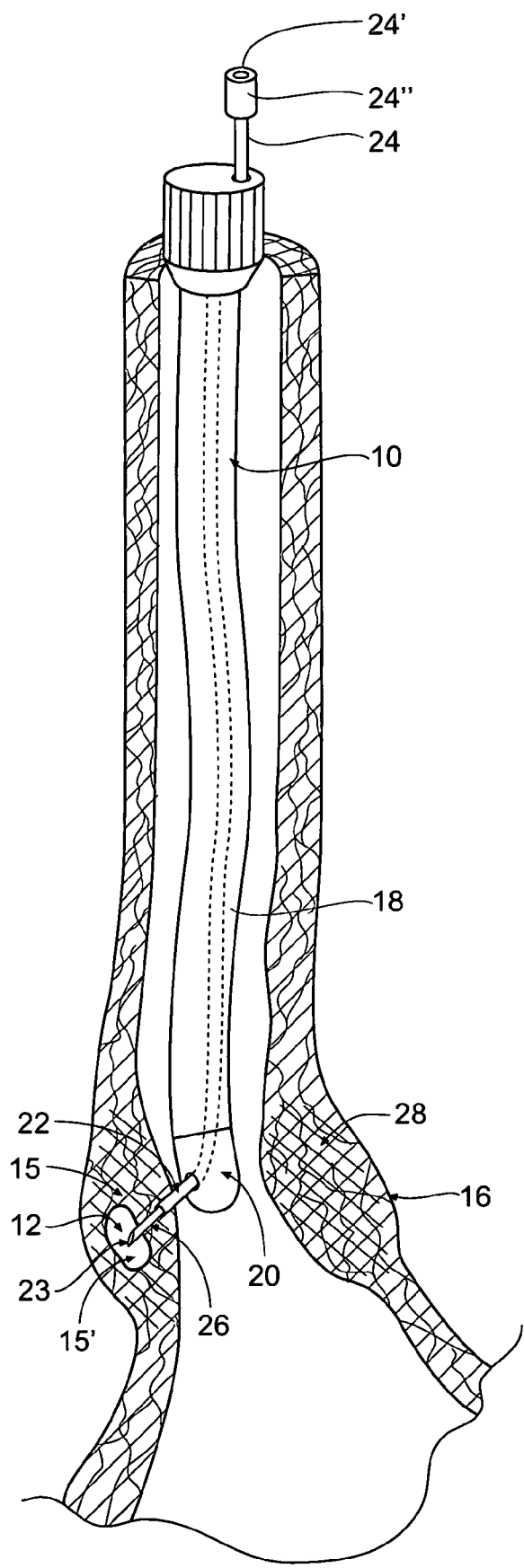
FIG. 1B is an illustrated lateral view of the upper GI tract illustrating the delivery of a polymer material into a treatment site in the sphincter wall.
Figure 2:
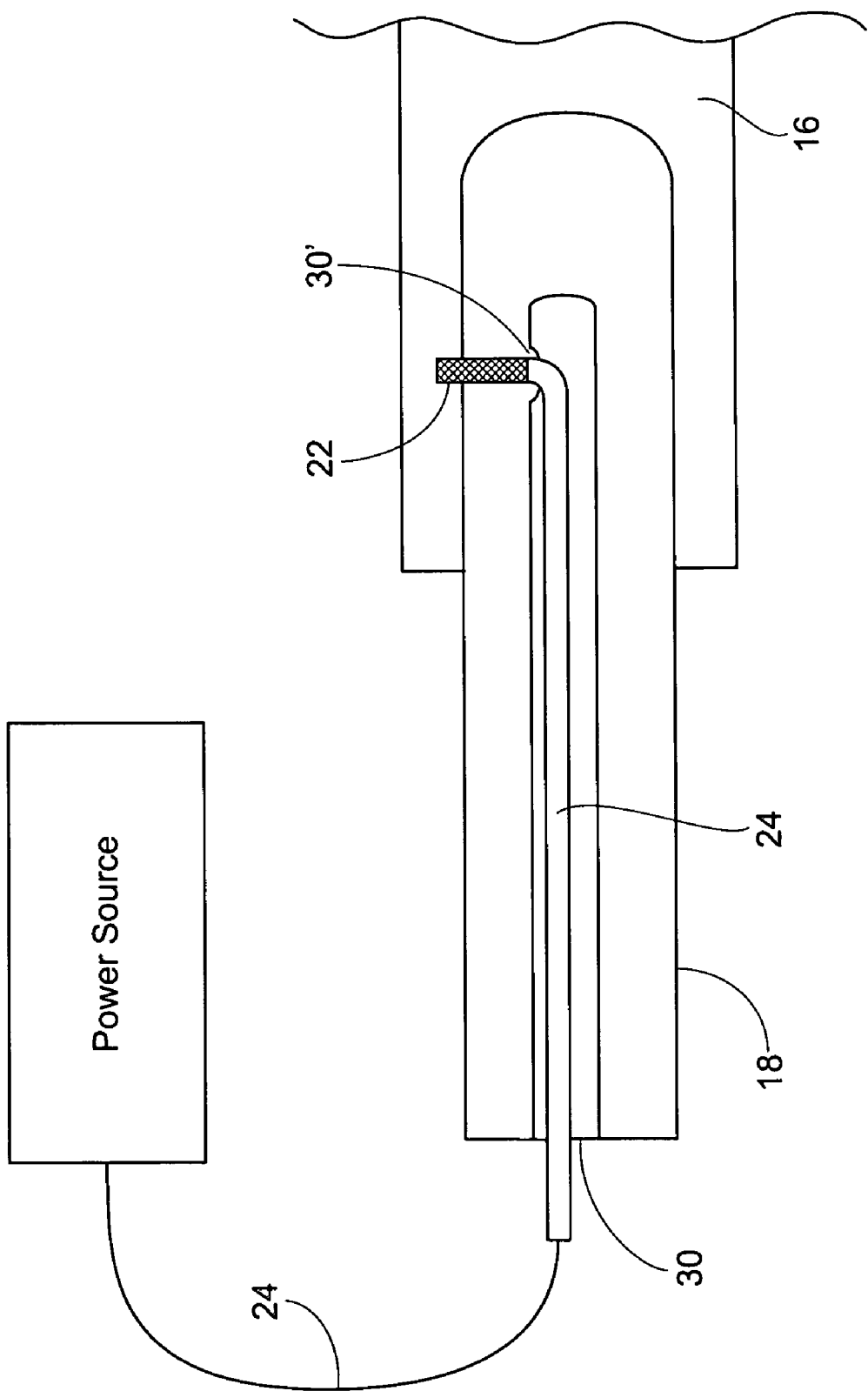
FIG. 2 is a lateral view of the present invention illustrating the catheter lumen, catheter end energy delivery device, cable and power supply.

Referring now to FIGS. 1A, 1B and 2, one embodiment of a sphincter treatment apparatus 10 delivers energy to a target tissue site 12, also called treatment site 12, to produce cell necrosis 14 in a sphincter 16, such as the lower esophageal sphincter (LES). In this embodiment, sphincter treatment apparatus 10 comprises a flexible elongate shaft 18, also called introducer 18, or catheter 18, with a distal extremity 20, also called catheter end 20, in turn coupled with one or more energy delivery devices 22. Energy delivery devices 22 are coupled to a guide wire 24 also called cable 24 and are also configured to be coupled to a power source. Energy delivery device 22 is coupled to a tissue piercing device 26, which can also be the distal end 26 of energy delivery device 22. Energy delivery device 22 and tissue piercing device 26 may both have a continuous internal lumen 23 that is fluidically coupled to a fluid lumen 24' in guide wire 24. Energy delivery device 22 and tissue piercing device 26 are configured to penetrate a fixed depth into a sphincter wall 28 and deliver energy to a portion thereof. In one embodiment tissue piercing device 26 is a hollow hypodermic needle 26 well known to those skilled in the art.

In one embodiment illustrated in FIG. 1B, tissue piercing device 26 is configured to penetrate a fixed depth into a sphincter wall 28 and deliver a polymer material 15 (also called polymer 15) via lumen 23 to a treatment site 12. Delivery of polymer 15 can be accomplished using an infusion pump or syringe (neither shown but both well known to those skilled in the art) fluidically coupled to tissue piercing device 26. Upon delivery of sufficient thermal energy from energy delivery device 22 to treatment site 12, the delivered polymer material 15', undergoes a curing and/or polymerization reaction well known to those skilled in the art whereby one or more of the following occurs: (i) crosslinks form between adjacent molecular chains of polymer 15, (ii) the molecular chains of polymer 15 contract along their linear/longitudinal axis resulting in a shortening or shrinkage of polymer 15 in one or more axises, (iii) the molecular chains of polymer 15 increase in length (iv) a viscoelastic property of delivered polymer 15 is altered (v) the viscosity of delivered polymer 15' is increased, and (vi) the stiffness of delivered polymer 15 is increased. As a result of one or more of these changes, all or a portion of delivered polymer 15' may undergo a transformation from a liquid or emulsion state to a less liquid or semisolid state. The portion of delivered polymer 15' that undergoes this reaction is called cured polymer 15" also called polymer particle 15". Suitable materials for polymer 15 include polysiloxanes (e.g. silicones), polyurethanes and collagen, all well known to those skilled in the art. Suitable geometries for polymer particle 15" include, but are not limited to, the following shapes: spherical, semispherical, oval and cylindrical. Suitable diameters for polymer particles 15" include a range from 0.01 to 0.5 inches.

Referring to FIG. 2, catheter end 20 is configured to be positionable in a sphincter 16 such as the LES or adjacent anatomical structure, such as the cardia of the stomach. Catheter 18 has sufficient length to position catheter end 20 in the LES and/or stomach using a trans-oral approach. Typical lengths for catheter 18 include, but are not limited to, a range of 40-180 cms. Suitable materials for catheter 18 include, but are not limited to, polyethylenes, polyurethanes, silicones other biocompatible polymers known to those skilled in the art. Energy delivery devices 22 can be in the form of needle electrodes, both solid or hollow, as is well known to those skilled in the art. In other embodiments, energy delivery device 22 can be conical, cylindrical, rectangular or any polyhedron; each of said shapes having a flat, rounded, beveled, or pointed tip. Suitable materials for energy delivery device 22 include a combination of one or more of the following: i) stainless and other steels suitable for electrode applications known to those skilled in the art, ii) alloys of gold, silver and platinum, iii) nickel-titanium alloys, or iv) other conductors known to those skilled in the art.

Catheter 18 may have one or more lumens 30, that extend the frill length of catheter 18, or only a portion thereof. Lumens 30 may be used as paths for cables, catheters, guide wires, pull wires, insulated wires, fluid and optical fibers. Lumens 30 may have one or more apertures 30' at or near distal catheter end 20. In one embodiment, lumens 30 (along with aperture 30') in catheter 18 are used as a guiding pathway for guidewire 24 to facilitate the positioning of tissue piercing device 26 at treatment site 12.

Guide wire 24 is configured to facilitate the positioning of energy delivery device 22 a selectable distance (1-4 mms) into the sphincter wall 28. Suitable materials and components for guide wire 24 include an insulated wire, an insulated guide wire, a plastic-coated stainless steel hypotube with internal wiring, or a catheter with internal wiring, all of which are known to those skilled in the art. Guide wire 24 may also have one or more lumens 24' which can be used to deliver fluid or gas. Also guide wire 24 may have one or more proximal fittings 24" (such as a luer fitting or lemo connector) for facilitating connection to fluid lines and electronic cabling.

Turning now to a discussion of energy-tissue interactions, energy flowing through sphincter or other tissue causes heating of the tissue due to absorption of the energy by the tissue. This heating can cause injury to the affected cells and can be substantial enough to cause cell death, a phenomenon also known as cell necrosis. The controlled delivery of energy by energy delivery device 22 results in controlled cell necrosis 14, also called lesions 14, at target tissue site 12.

Suitable energy devices and power sources for energy delivery device 22 include the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, or (xii) combinations of any of the above. For ease of discussion for the remainder of this application, the power source utilized is an RF source and energy delivery device 22 is one or more RF electrodes 22, also described as electrodes 22. However, all of the other herein mentioned power sources and energy delivery devices are equally applicable to sphincter treatment apparatus 10.

Figure 3:
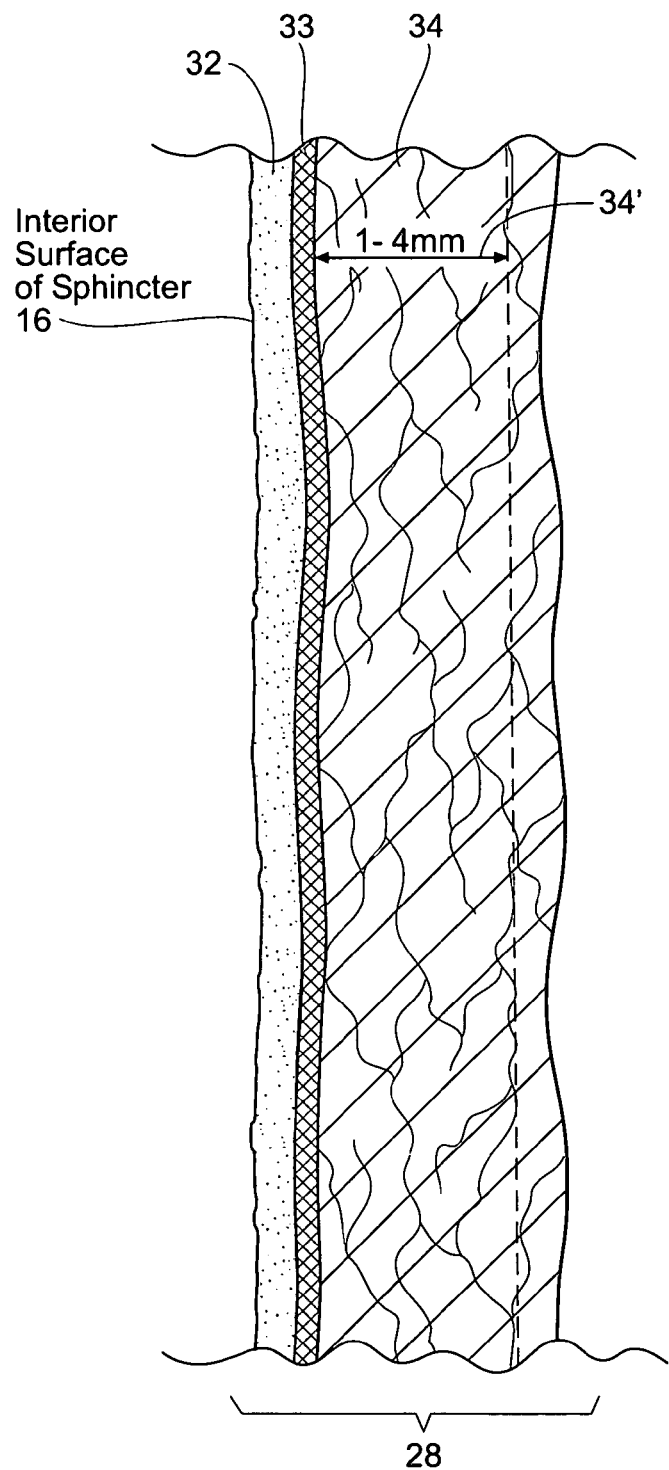
FIG. 3 depicts a cross sectional view of sphincter anatomy illustrating the layers of the sphincter wall.

Turning now to a discussion of sphincter anatomy (depicted in FIG. 3), the first several layers of sphincter 16 consist of a mucosal layer 32, a submucosal layer 33 and an underlying smooth muscle collagen tissue layer 34. RF electrode 22 is configured to produce controlled cell necrosis or lesions 14 in smooth muscle collagen tissue layer 34 underlying mucosal and submucosal layers 32 and 33. More specifically, RF electrode 22 is configured to produce controlled cell necrosis 14 in the portion of smooth muscle collagen tissue 34' that lies approximately 1-4 nuns from the surface of mucosal layer 32.

Figure 4A:
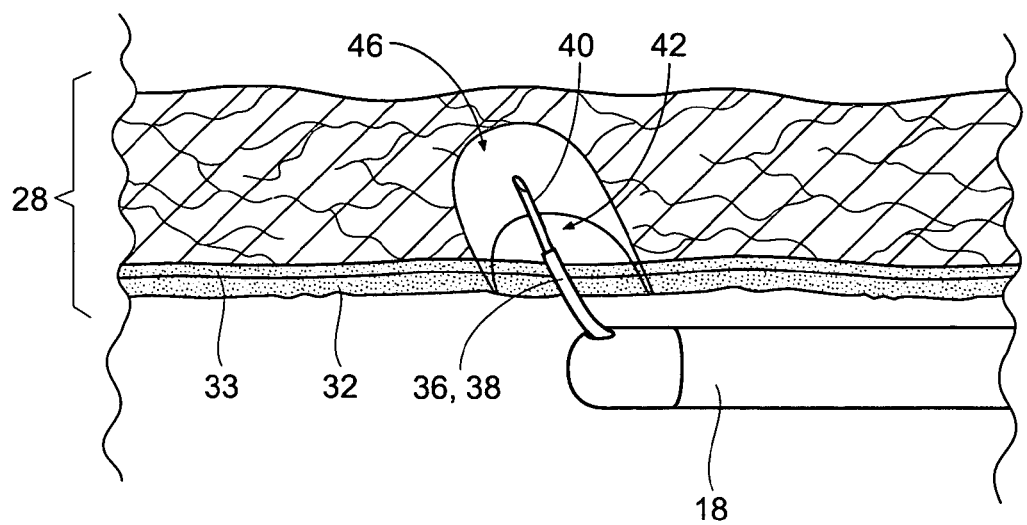
FIG. 4A is a lateral view of the RF electrode and sphincter wall, illustrating insulated and exposed electrode segments and the creation of a protected site.

Referring now to FIG. 4A, RF electrode 22 has an insulator 36, covering the exterior of an insulated segment 38 except for an exposed segment 40. For purposes of this disclosure, an insulator is a barrier to either thermal or electromagnetic energy flow. As shown in FIG. 4A, insulated segment 38 is of sufficient length to extend into sphincter wall 28 and minimize the transmission of energy and subsequent injury to a protected site 42 near or adjacent to insulated segment 38. Typical lengths for insulated segment 38 include, but are not limited to, 1-4 mms. Suitable materials for insulator 36 include, but are not limited to, polytetrafluoroethylene (Teflon®), polyimides, polyamides and other insulating polymers known to those skilled in the art.

Figure 4B:
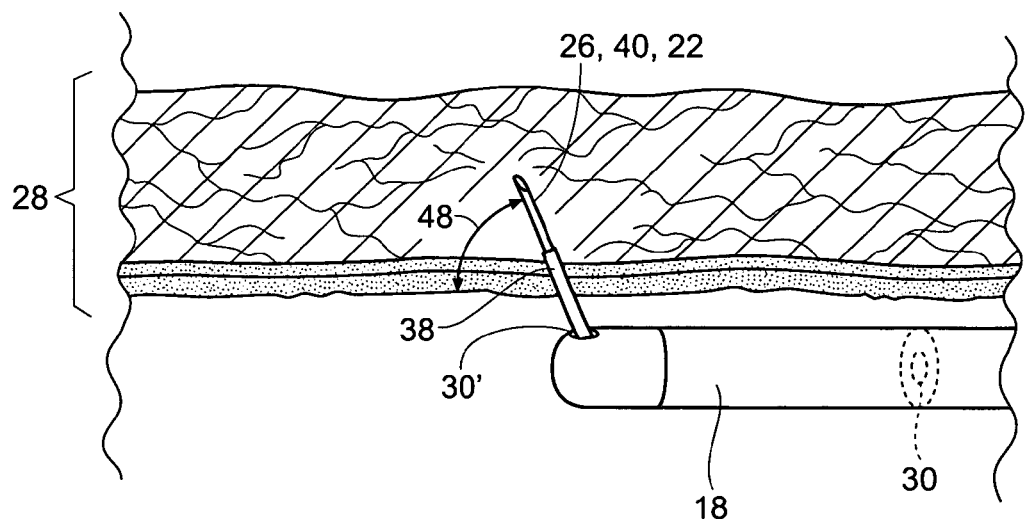
FIG. 4B is a lateral view of the RF electrode and sphincter wall, illustrating apertures in the catheter which are used to control the penetration angle of the tissue piercing device in a sphincter wall.

Referring now to FIG. 4B, in one embodiment lumens 30 and apertures 30' are of sufficient diameter to allow the free movement of guidewire 24 in catheter 18 so as to be able to controllably position tissue piercing device 26 to a selected depth into sphincter wall 28. Apertures 30' can be configured so as to control the angle of penetration 48 (also called penetration angle 48 emergence angle 48) that tissue piercing device 26 makes with sphincter wall 28. Apertures 30' can be further configured so as to maintain penetration angle 48 constant (or near constant) during the insertion of tissue piercing device 26 into sphincter wall 28 so as to minimize tearing or unnecessary trauma to sphincter wall tissue. In various embodiments, the emergence angle 48 of apertures 30' which can vary from 1 to 90°.

Figure 5:
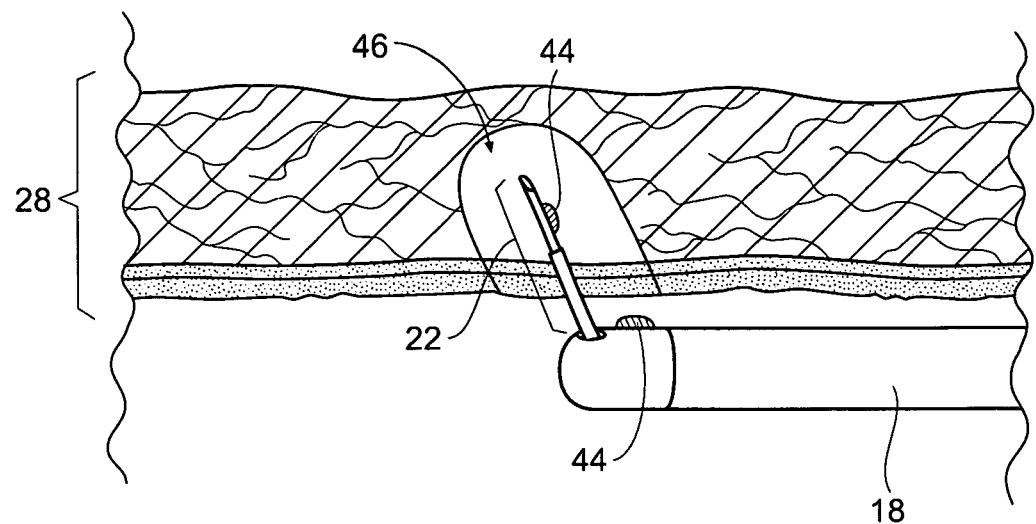
FIG. 5 is an enlarged lateral view illustrating the placement of sensors on/adjacent the energy delivery device/RF electrode.

Referring now to FIG. 5, one or more sensors 44 can be coupled to RF electrode 22 for sensing the temperature of sphincter tissue at target tissue site 12. More specifically, sensors 44 permit accurate determination of the surface temperature of sphincter wall 28 at an electrode tissue interface 46. This information can be used to regulate both the delivery of energy and cooling medium to the interior surface of sphincter wall 28 as will be discussed herein. Sensors 44 can be positioned on or adjacent to RF electrode 22. Suitable sensors that may be used for sensor 44 include: thermocouples, fiber optics, resistive wires, thermocouple IR detectors, and the like. Suitable thermocouples for sensor 44 include: T type with copper constantene, J type, E type and K types as are well known those skilled in the art.

Figure 6:
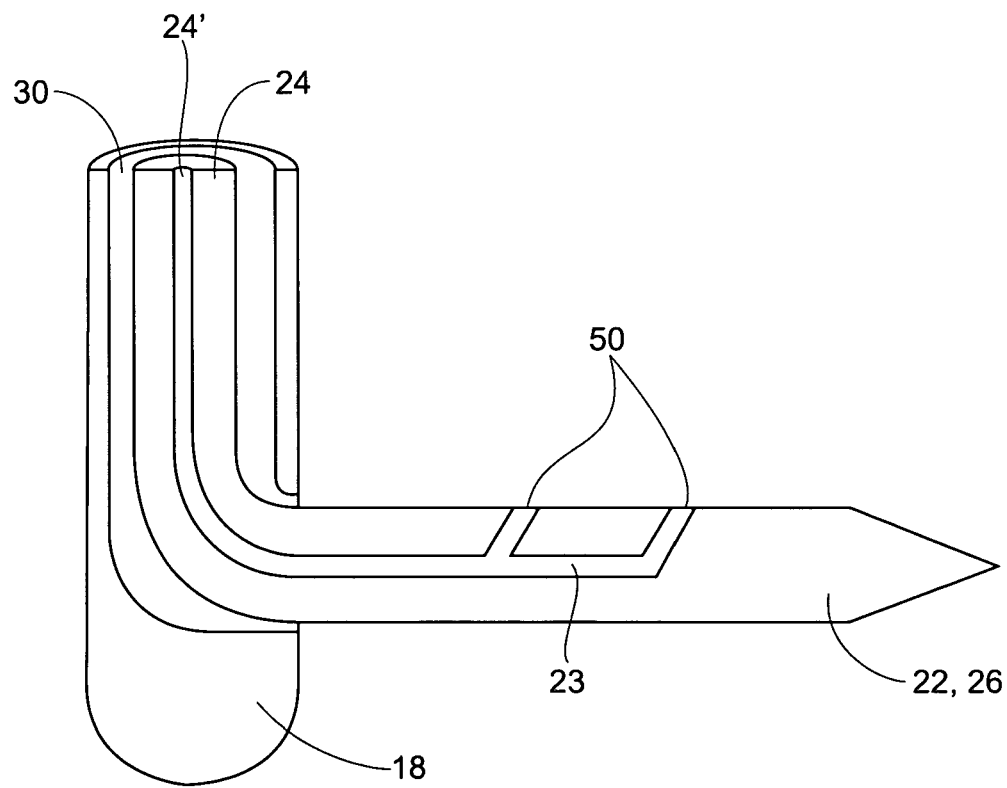
FIG. 6 is a cross sectional view illustrating the use of a fluid introduction lumen and aperture in the energy delivery device/RF electrode for delivery of a cooling medium.

Referring now to FIG. 6, RF electrode 22 includes a fluid introduction lumen 23, that may be coupled with catheter lumen 30. These coupled lumens provide a path for the delivery of a fluid, such as a cooling or electrolytic fluid (which will be discussed herein), to electrode tissue interface 46 or another site. As shown in FIG. 6, fluid introduction lumen 23 may include an aperture 50 on the distal portion of RF electrode 22.

Figure 7:
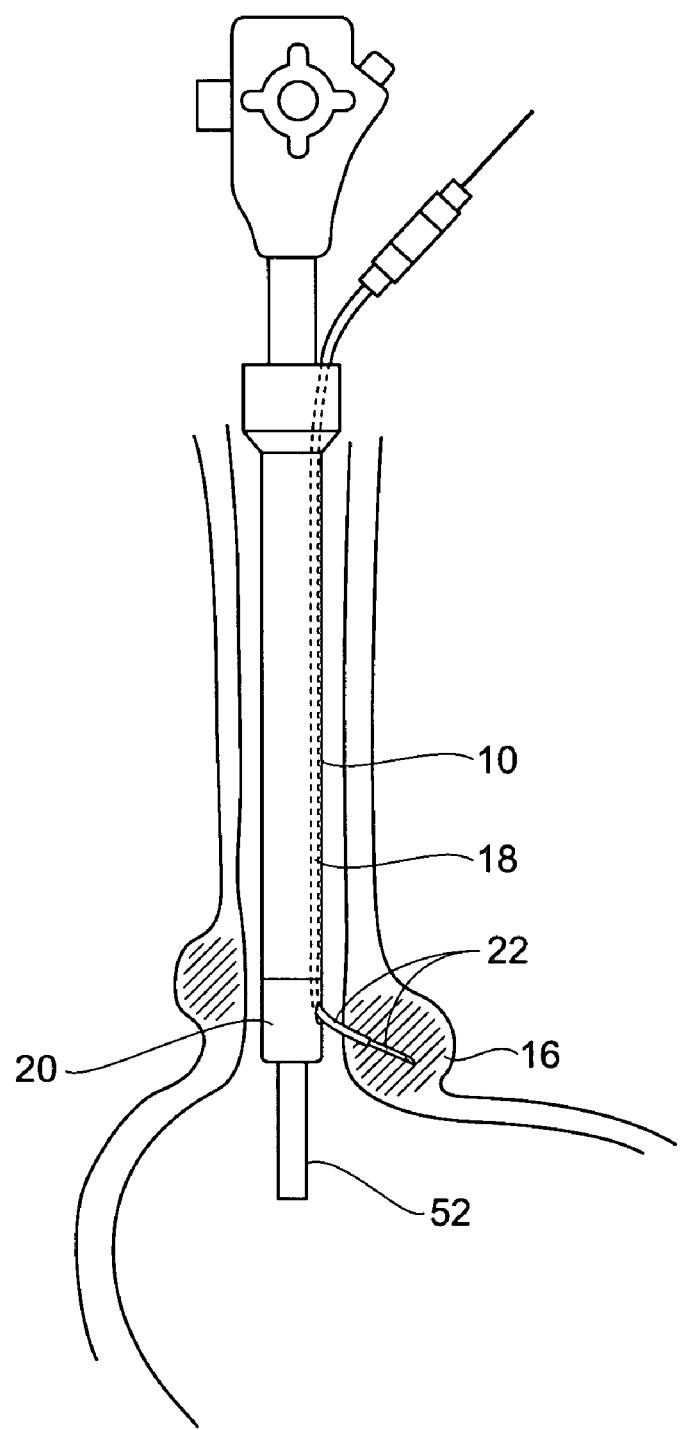
FIG. 7 is a cross sectional view illustrating a visualization device coupled to an embodiment of the invention.

Referring now to FIG. 7, another embodiment of sphincter treatment apparatus 10 includes a visualization device 52 which can include a combination of one or more of the following: a viewing scope, an expanded eyepiece, fiber optics (both imaging and illuminating fibers), video imaging and the like.

Figure 8:
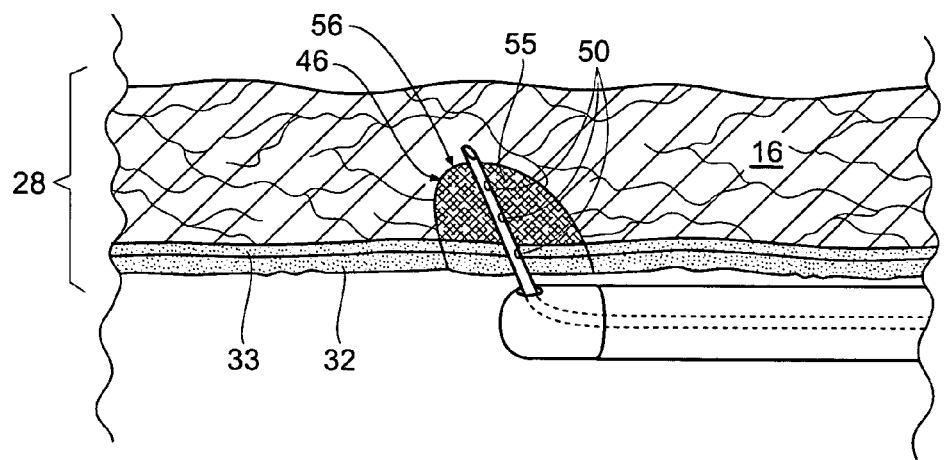
FIG. 8 is a lateral view of the sphincter wall illustrating the use of cooling medium to create cooled zones at the electrode-tissue interface.
Figure 9:
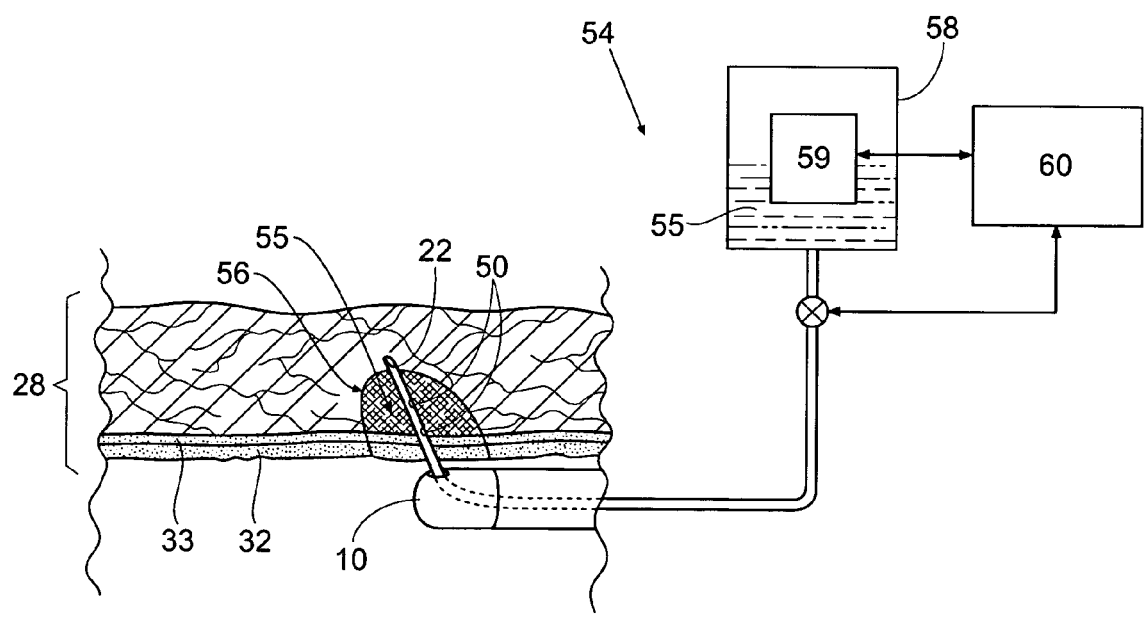
FIG. 9 depicts the flow path and fluid connections employed to deliver cooling medium to the energy delivery device/RF electrode and/or electrode-tissue interface.

It may be desirable to employ a cooling system 54 coupled to energy delivery device 22 to cool all or a portion of energy-delivery device 22 and the area near electrode tissue interface 46 before, during or after the delivery of energy in order to reduce the degree and area of cell injury in the tissue adjacent electrode tissue interface 46. As shown in FIG. 8, the use of cooling protects against, or otherwise reduces the degree of, cell damage to cooled zone 56 in the vicinity of aperture 50 and/or electrode tissue interface 46 which will preferably include mucosal and submucosal layers 32 and 33. In one embodiment shown in FIG. 9, cooling system 54 can include one or more of the following: i) a cooling medium 55 (which can be a liquid or a gas) that is delivered to RF electrode 22 via aperture 50 and flow-controlled via a feedback control system 60 discussed herein, ii) a cooling medium reservoir 58 coupled to aperture 50, and iii) a cooling device 59 (which may be integral to fluid reservoir 58) coupled to cooling medium 55 and controlled via a feedback control system 60 discussed herein. In another embodiment, cooling medium 55 can be introduced via apertures 50 or semipermeable membranes located in one or more locations on sphincter treatment apparatus 10 in communication with reservoir 58 and thermal communication with cooling device 59. In yet another embodiment, cooling medium 55 can be introduced externally to RF electrode 22. In still another embodiment, cooling medium 55 is thermally coupled to RF electrode 22 and/or electrode tissue interface 46. In yet another embodiment, cooling device 59 (such as a Peltier effect device or heat pipe) is thermally coupled to RF electrode 22 and/or electrode tissue interface 46.

Figure 10:
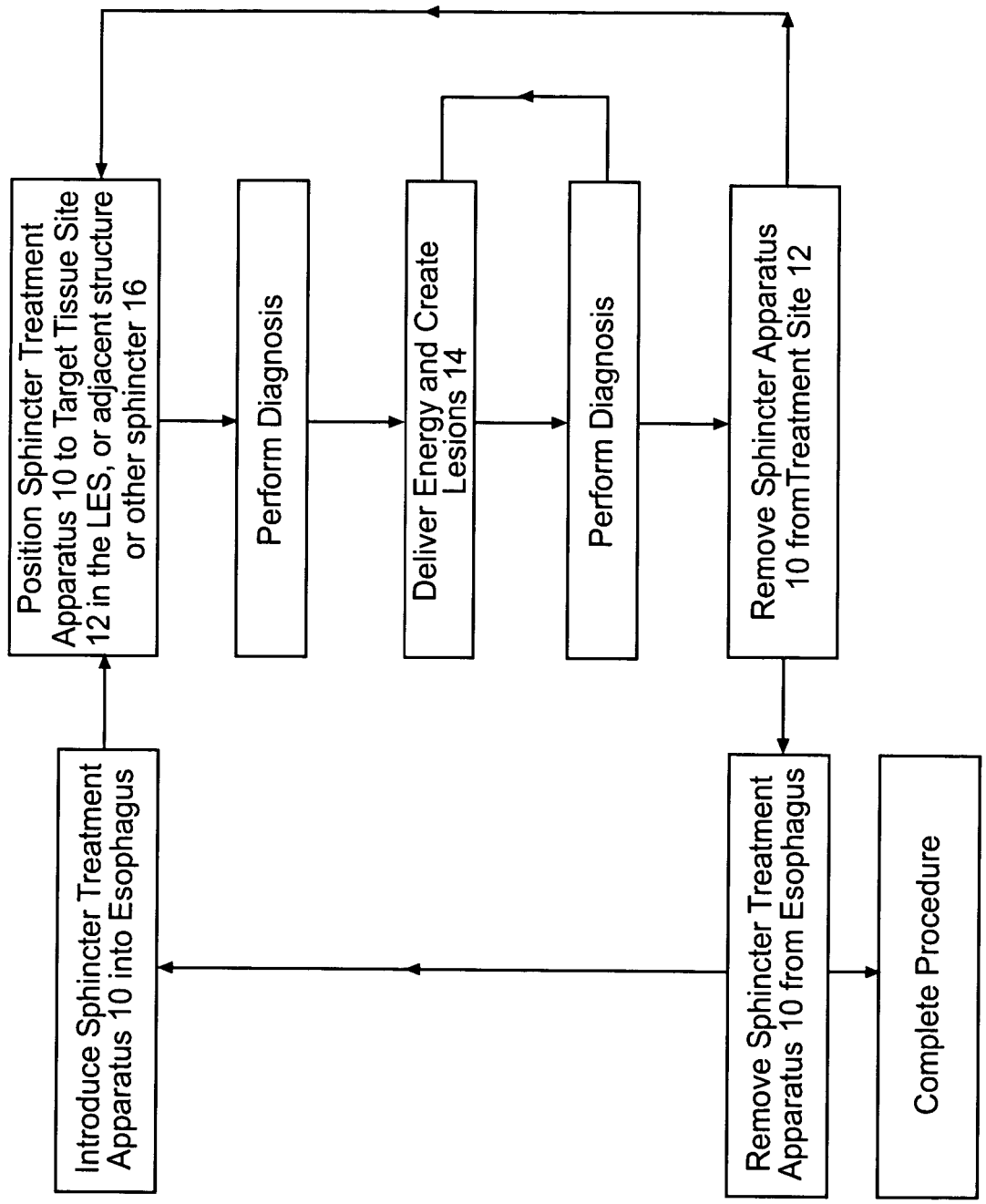
FIG. 10 is a flow chart illustrating a sphincter treatment method.

FIG. 10 is a flow chart illustrating a method for using sphincter treatment apparatus 10. In this embodiment, sphincter treatment apparatus 10 is first introduced into the esophagus under local anesthesia and positioned at target tissue site 12. Sphincter treatment apparatus 10 can be introduced into the esophagus by itself or through a lumen in an endoscope (not shown), such as disclosed in U.S. Pat. Nos. 5,448,990 and 5,275,608, incorporated herein by reference, or a similar esophageal access device known to those skilled in the art.

Figure 11:
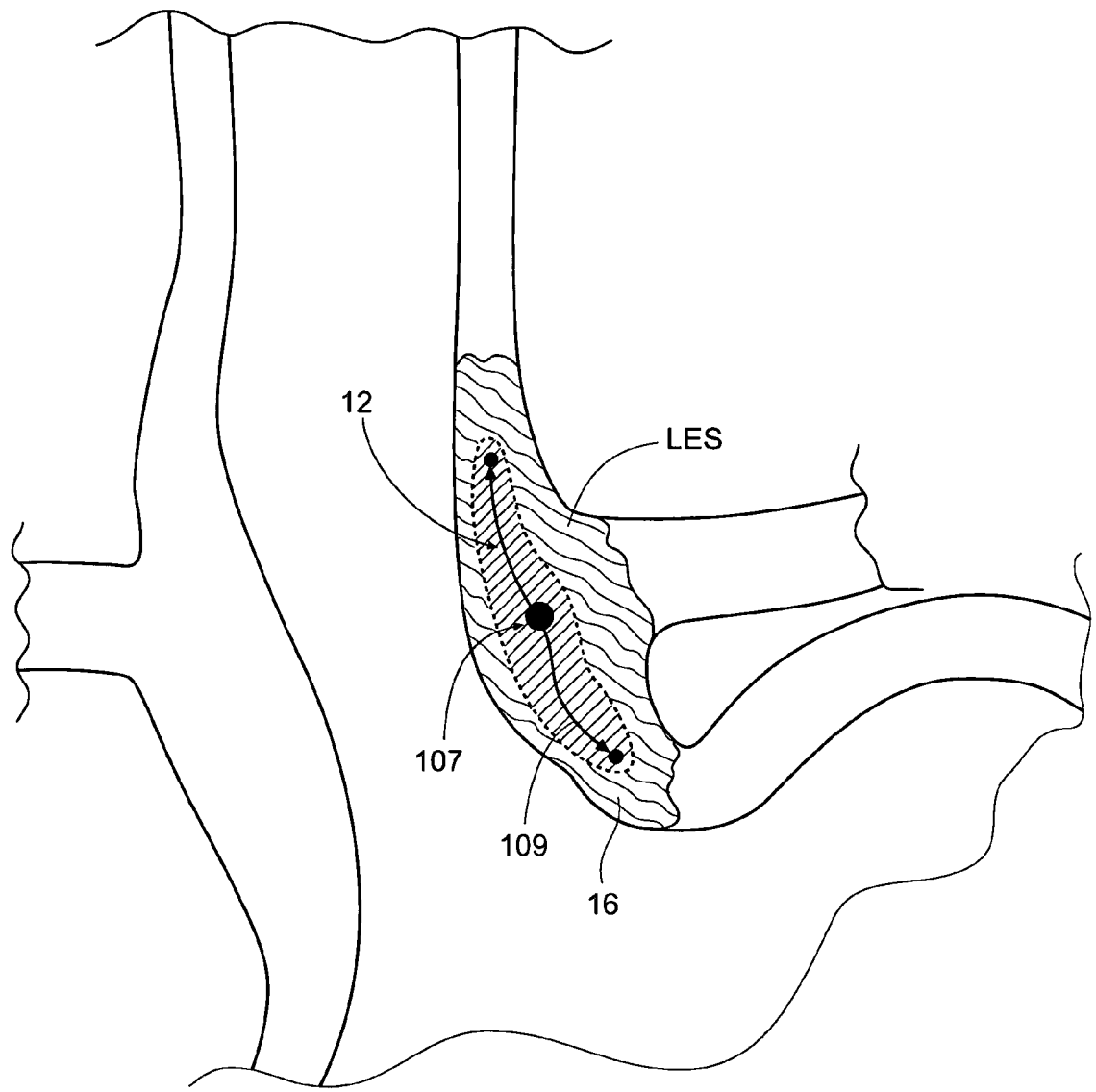
FIG. 11 is a lateral view of sphincter smooth muscle tissue illustrating electrical foci and electrically conductive pathways for the origination and conduction of aberrant electrical signals in the smooth muscle of the lower esophageal sphincter or other tissue.

The diagnostic phase of the procedure then begins and can be performed using a variety of diagnostic methods, including, but not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated, (iii) impedance measurement to determine the electrical conductivity between the esophageal mucosal layers and sphincter treatment apparatus 10, and (iv) measurement and surface mapping of the electropotential of the LES during varying time periods which may include such events as depolarization, contraction and repolarization of LES smooth muscle tissue. This latter technique is done to determine target tissue sites 12 in the LES or adjoining anatomical structures that are acting as electrical foci 107 or electrically conductive pathways 109 for abnormal or inappropriate polarization and relaxation of the smooth muscle of the LES (Refer to FIG. 11).

After diagnosis, the treatment phase of the procedure then begins. In this phase of the procedure the delivery of energy to target tissue site 12 can be conducted under feedback control (described herein), manually or by a combination of both. Feedback control enables sphincter treatment apparatus 10 to be positioned and retained in the esophagus during treatment with minimal attention by the physician. Feedback can be included and is achieved by the use of one or more of the following methods: (i) visualization, (ii) impedance measurement, (iii) ultrasonography, (iv) temperature measurement and, (v) sphincter contractile force measurement via manometry. A second diagnostic phase may be included after the treatment is completed. This provides an indication of LES tightening treatment success, and whether or not a second phase of treatment, to all or only a portion of the esophagus, now or at some later time, should be conducted. The second diagnostic phase is accomplished through, (i) visualization, (ii) measuring impedance, (iii) ultrasonography, (iv) temperature measurement, or (v) measurement of LES tension and contractile force via manometry. It will be appreciated that the above procedure is applicable in whole or part to the treatment of other sphincters in the body.

Figure 12:
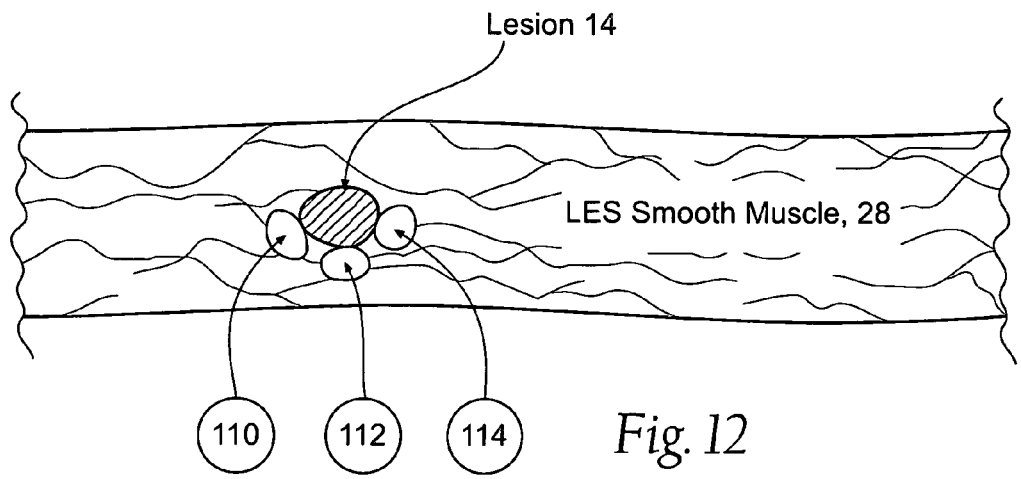
FIG. 12 is a lateral view of a sphincter wall illustrating the infiltration of tissue healing cells into a lesion in the smooth tissue of a sphincter following treatment with the sphincter treatment apparatus of the present invention.
Figure 13:
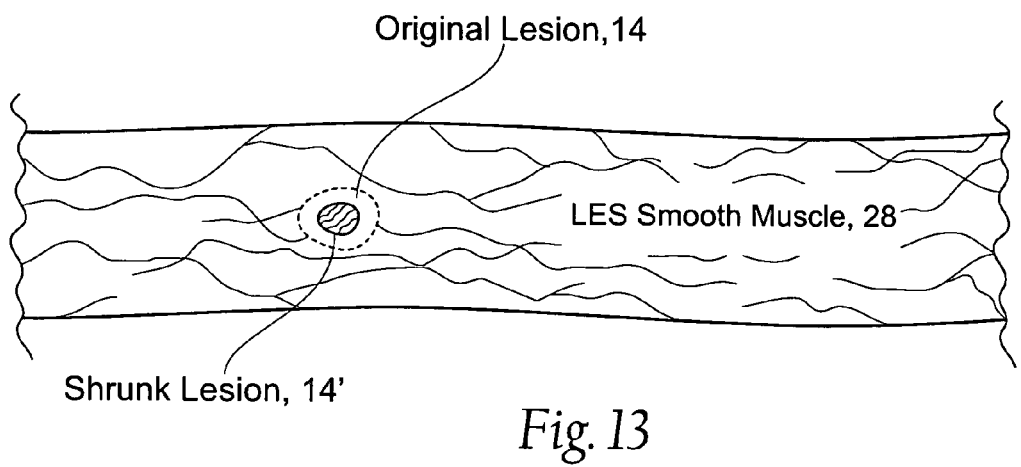
FIG. 13 is a view similar to that of FIG. 12 illustrating shrinkage of the lesion site caused by cell infiltration.

The area and magnitude of cell injury in the LES or sphincter 16 can vary. However, it is desirable to deliver sufficient energy to the targeted tissue site 12 to be able to achieve tissue temperatures in the range of 55-95° C. and produce lesions 14 at depths ranging from 1-4 mms from the interior surface of the LES or sphincter wall 28. It is also desirable to deliver sufficient energy such that the resulting lesions 14 have a sufficient magnitude and area of cell injury to cause an infiltration and/or proliferation of lesion 14 by fibroblasts 110, myofibroblasts 112, macrophages 114 and other cells involved in the tissue healing process (refer to FIG. 12). As shown in FIG. 13, these cells cause a contraction of tissue around lesion 14, decreasing its volume and/or altering the biomechanical properties at lesion 14 so as to result in a tightening of LES or sphincter 16. These changes are reflected in transformed lesion 14' shown in FIG. 13.

It is desirable that lesions 14 are predominantly located in the smooth muscle collagen layer of selected sphincter 16 at the depths ranging from 1 to 4 mms from the interior surface of sphincter wall 28.

Figure 14:
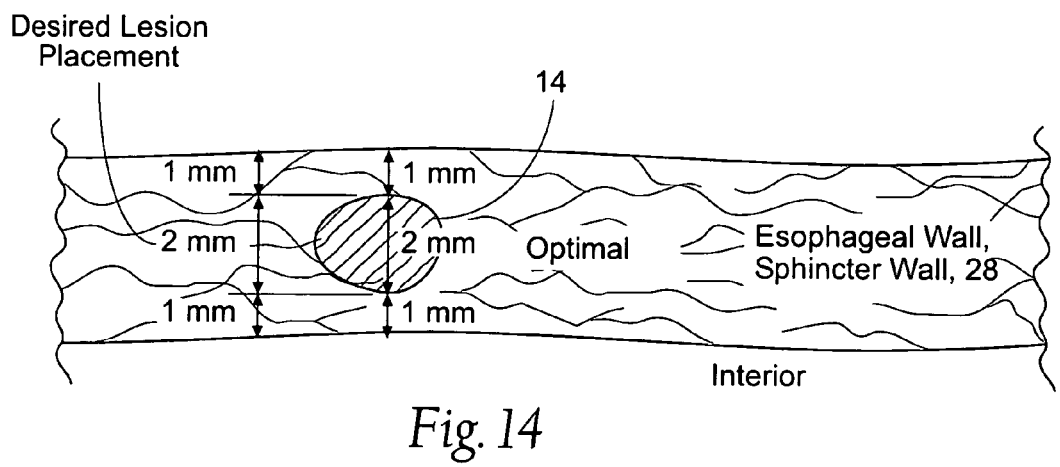
FIG. 14 is a lateral view of the esophageal wall illustrating the preferred placement of lesions in the smooth muscle layer of an esophageal sphincter.

Accordingly, the diameter of lesions 14 can vary between 0.1 to 4 mms. It is preferable that lesions 14 are less than 4 mms in diameter in order to reduce the risk of thermal damage to the mucosal layer. In one embodiment, a 2 mm diameter lesion 14 centered in the wall of the smooth muscle collagen layer provides a 1 mm buffer zone to prevent damage to the mucosa, submucosa and adventitia, while still allowing for cell infiltration and subsequent sphincter tightening on approximately 50% of the thickness of the wall of the smooth muscle collagen layer (refer to FIG. 14). Also, lesions 14 can vary both in number and position within sphincter wall 28. Once treatment is completed, sphincter treatment apparatus 10 is withdrawn from the esophagus or other sphincter 16. This results in the LES or other sphincter returning to approximately its pretreatment state and diameter.

Figure 15:
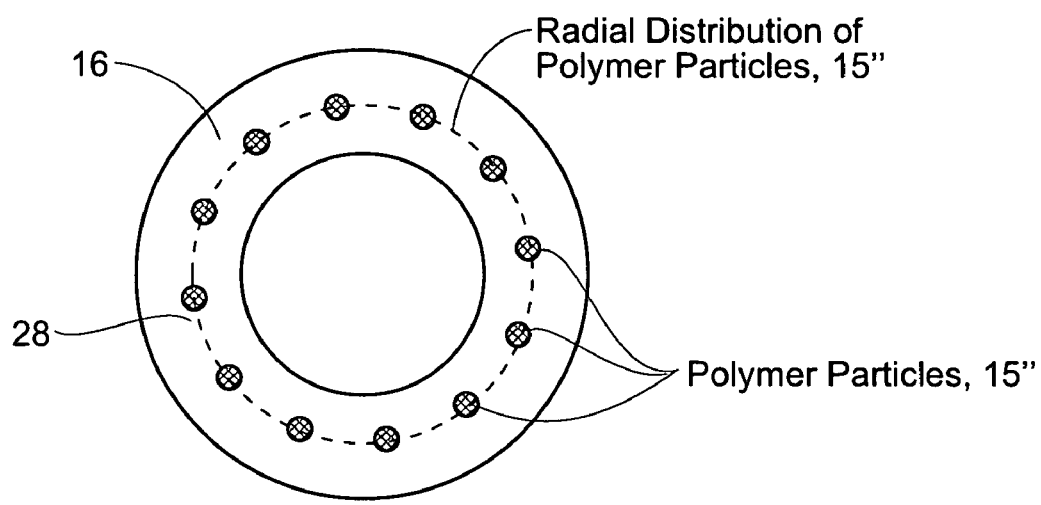
FIG. 15 is a lateral view illustrating a radial distribution of cured polymer particles used to increase sphincter wall thickness and decrease sphincter inner diameter.

Referring now to FIG. 15, in one embodiment polymer particles 15" can be distributed in a variety of patterns in sphincter wall 28 including a radial distribution at even depths along a radial axis of sphincter 16. Other distributions not shown include: (i) a wavy or folded circle of polymer particles 15" at varying depths in sphincter wall 28 evenly spaced along the radial axis of sphincter 16, (ii) polymer particles 15"' randomly distributed at varying depths, but evenly spaced in a radial direction; and, (iii) an eccentric pattern of polymer particles 15" in one or more radial locations in sphincter wall 28. The pattern of and diameter of polymer particles 15" can be selected to controllably increase the thickness 28' of sphincter wall 28 and/or decrease the inner diameter 16' of sphincter 16.

Figure 16:
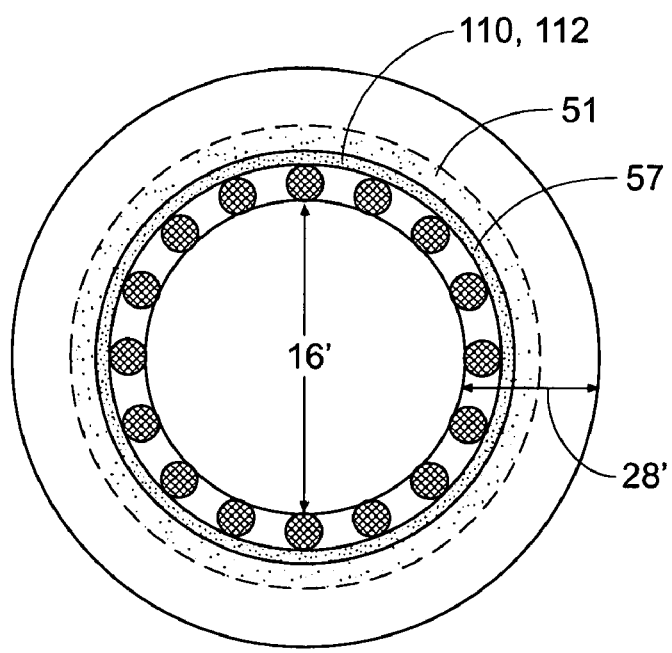
FIG. 16 is a lateral view illustrating the use of a band of shrunk collagen surrounding and mechanically supporting a radial distribution of cured polymer particles.

Referring now to FIG. 16, RF energy can be delivered to sphincter wall 28 to shrink native collagen 51 within the smooth muscle collagen tissue layer 34 of sphincter wall 28 so as to create a supporting band 57 of tightened collagen in contact with one or more of polymer particles 15" distributed along a radial axis of sphincter 16. Band 57 serves to both mechanically link and mechanically support polymer particles 15". This serves one or more of the following functions: (i) distribution of the stresses within sphincter wall 28, (ii) retention of the desired placement of polymer particles 15" within sphincter wall 28; and, (iii) maintenance of improvements in the tension and inner diameter of sphincter wall 28. Also band 57 can be selectively shrunk so as to selectively tighten sphincter 16 and decrease inner sphincter diameter 16'. In another embodiment, band 57 can be composed of fibroblasts 110, myofibroblasts 112 and other tissue healing cells.

Figure 17:
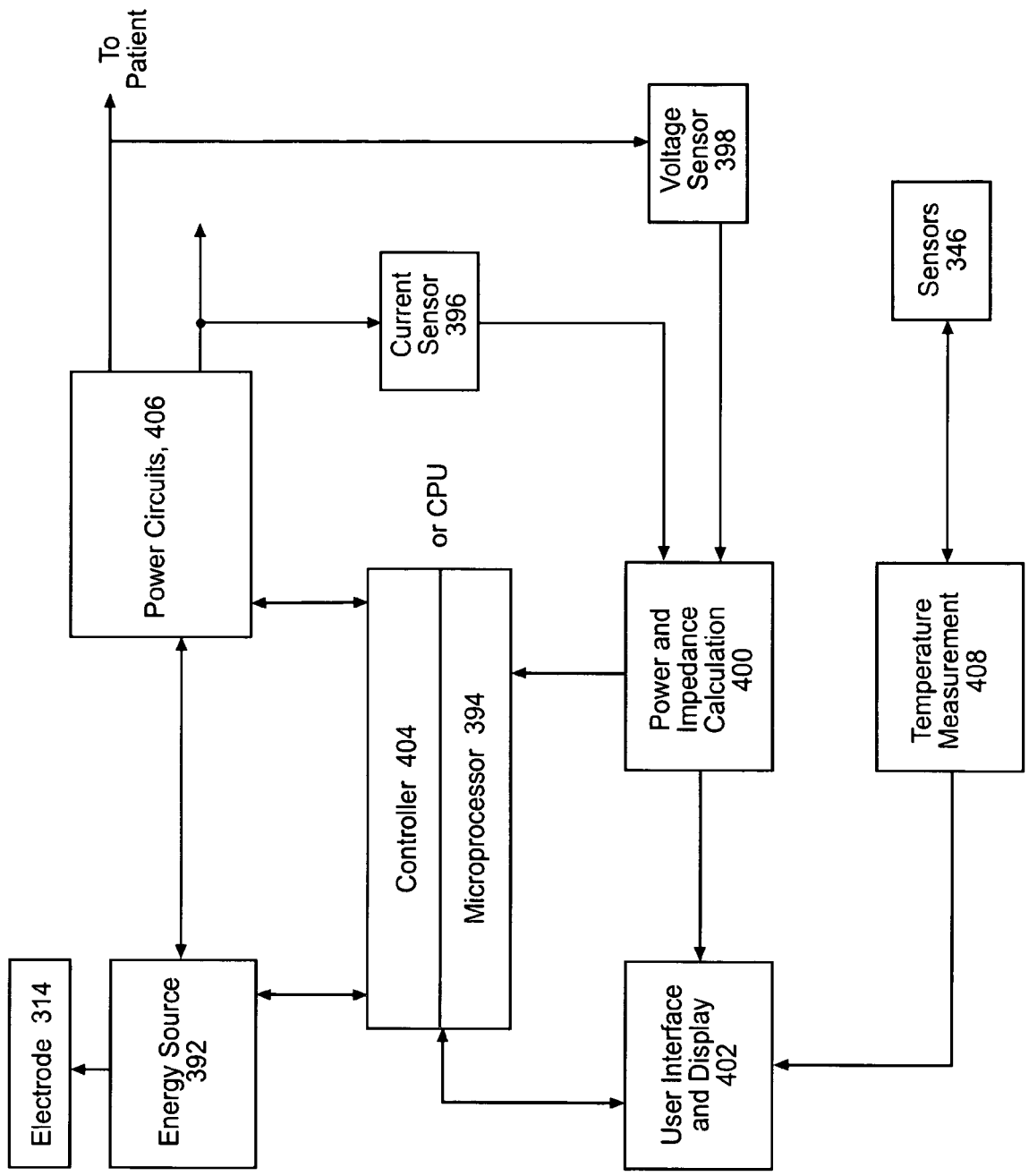
FIG. 17 depicts a block diagram of the feed back control system that can be used with the sphincter treatment apparatus.

In one embodiment, elements of sphincter treatment apparatus 10 are coupled to an open or closed loop feedback control system 60. Referring now to FIG. 17, an open or closed loop feedback system 60 couples sensor 346 to energy source 392. In this embodiment, electrode 314 is one or more RF electrodes 314. The temperature of the tissue, or of RF electrode 314, is monitored, and the output power of energy source 392 adjusted accordingly. The physician can, if desired, override the closed or open loop system 60. A microprocessor 394 can be included and incorporated in the closed or open loop system to switch power on and off, as well as modulate the power. The closed loop system 60 utilizes microprocessor 394 to serve as a controller, monitor the temperature, adjust the RF power, analyze the result, refeed the result, and then modulate the power.

With the use of sensor 346 and feedback control system 60, tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized. The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 18:
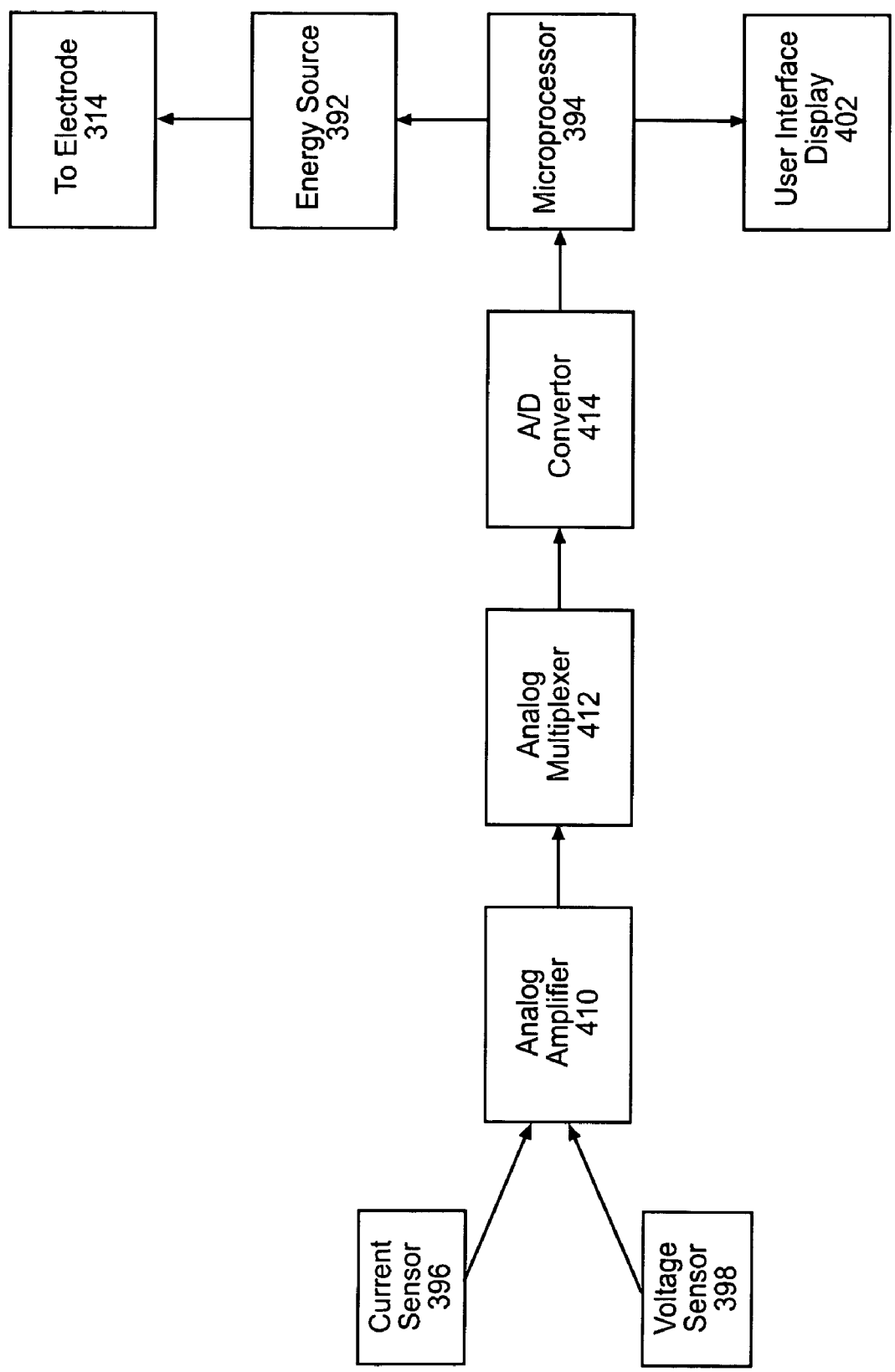
FIG. 18 depicts a block diagram of an analog amplifier, analog multiplexer and microprocessor used with the feedback control system of FIG. 17.

Referring now to FIG. 18, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 19:
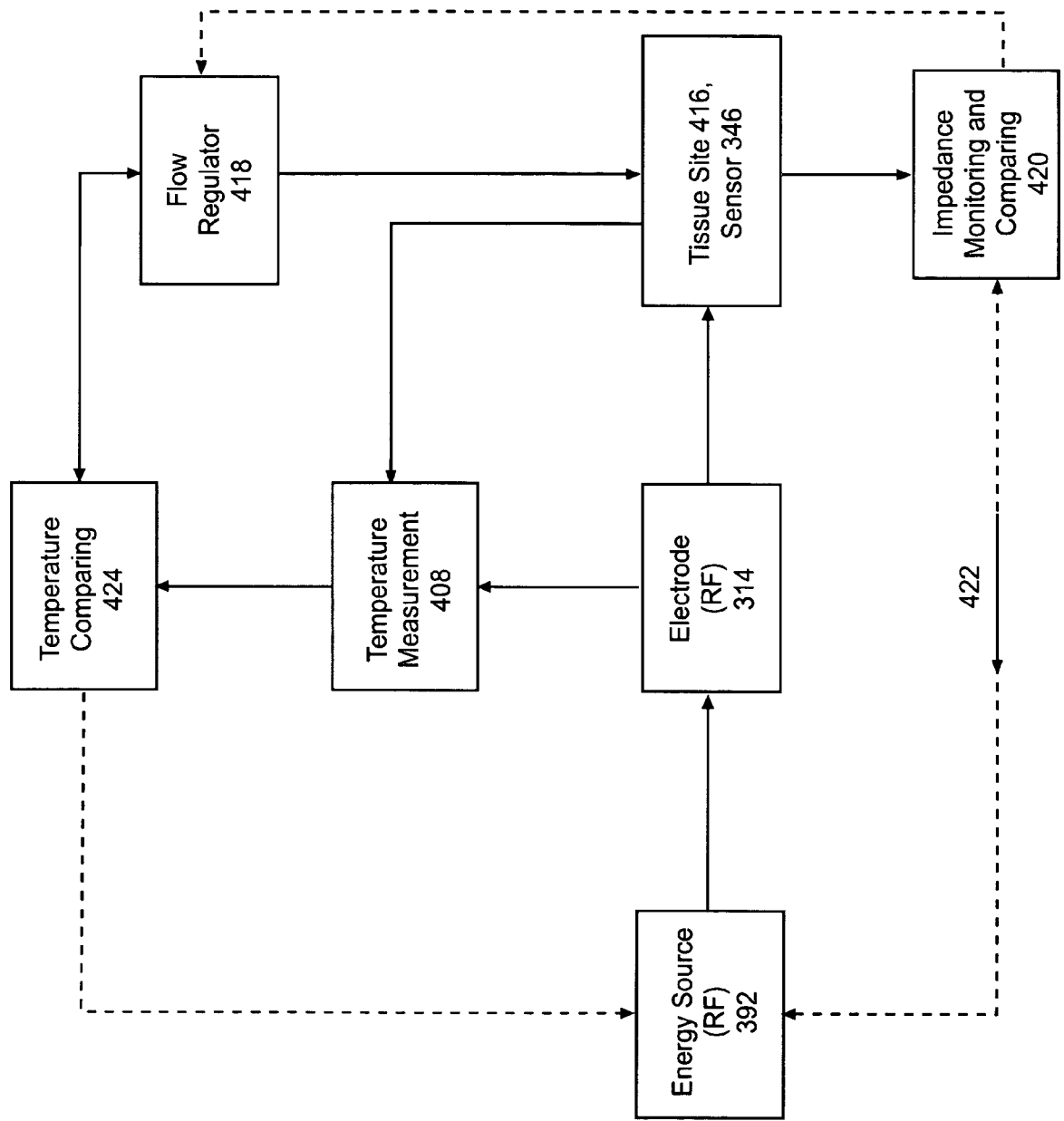
FIG. 19 depicts a block diagram of the operations performed in the feedback control system depicted in FIG. 17.

FIG. 19 illustrates a block diagram of a temperature and impedance feedback system that can be used to control the delivery of energy to tissue site 416 by energy source 392 and the delivery of cooling medium 55 to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to RF electrode 314.

The control of cooling medium 55 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the measured temperature has not exceeded the desired temperature, comparator 424 sends a signal to flow regulator 418 to maintain the cooling solution flow rate at its existing level. However if the tissue temperature is too high, comparator 424 sends a signal to a flow regulator 418 (connected to an electronically controlled micropump, not shown) representing a need for an increased cooling solution flow rate.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

We claim:

1. A method for treating a tissue region at or near a sphincter comprising
    (i) selecting at least one liquid polymer material that, upon exposure to thermal energy, cures to a less liquid or semi-solid state,
    (ii) providing a source of the at least one liquid polymer material,
    (iii) deploying a catheter carrying on its distal end a tissue-piercing element adjacent a tissue region at or near a sphincter,
    (iv) coupling the catheter to the source of the at least one liquid polymer material,
    (v) applying through the tissue-piercing element the at least one liquid polymer material into the tissue region,
    (vi) delivering thermal energy to the tissue piercing device to cure the liquid polymer material and form an array of spaced-apart polymer material particles in the tissue region,
    (vii) measuring tension and contractile force at the sphincter after formation of the array of spaced-apart polymer material particles in the tissue region to generate feedback indicative of sphincter tightening, and
    (viii) repeating (v), (vi), and (vii) if the feedback does not meet prescribed criteria.

2. A method according to claim 1, further including delivering energy to the tissue piercing device to create controlled cell necrosis.

3. A method according to claim 1, further including providing a cooling medium, and
conveying the cooling medium into contact with exterior sphincter tissue surface pierced by the tissue piercing device.

4. A method according to claim 1 wherein the polymer material comprises collagen.

5. A method according to claim 1 wherein the polymer material comprises silicone.

6. A method according to claim 1 wherein the array of spaced-apart polymer material is distributed at even depths along a radial axis of the sphincter.

7. A method according to claim 1 wherein the array of spaced-apart polymer material is distributed at varying depths m the tissue region.

8. A method according to claim 1 wherein the array of spaced-apart polymer material is evenly-spaced along a radial axis of the sphincter.

9. A method according to claim 2 wherein the delivery of energy shrinks native collagen to create a supporting band of tightened collagen in contact with one or more of the polymer material particles.

10. A method according to claim 9 wherein the band mechanically links the polymer material particles.

11. A method according to claim 9 wherein the band mechanically supports the polymer material particles.

12. A method according to claim 9 wherein the band distributes stresses within a sphincter wall.

13. A method according to claim 9 wherein the band retains a desired placement of the polymer material particles within a sphincter wall.

14. A method according to claim 9 wherein the band maintains improvements in at least one of tension and an inner diameter of a sphincter wall.

15. A method according to claim 9, further comprising selectively shrinking the band.

16. A method according to claim 9 wherein the band comprises at least one of fibroblasts, myofibroblasts, and other tissue healing cells.

17. A method according to claim 1 wherein (vii) includes sphincter contractile force measurement via manometry.

* * * * *